(12) United States Patent
Muratidi et al.

(10) Patent No.: US 11,913,598 B2
(45) Date of Patent: Feb. 27, 2024

(54) FALL ARRESTER DEVICE FOR A MEDICAL CARRYING SYSTEM, CARRYING SYSTEM FOR A PIECE OF MEDICAL EQUIPMENT, METHOD FOR ATTACHING A FALL ARRESTER DEVICE TO A CARRYING SYSTEM

(71) Applicant: Ondal Medical Systems GmbH, Hünfeld (DE)

(72) Inventors: Georg Muratidi, Oberaula (DE); Stefan Perplies, Hünfeld (DE)

(73) Assignee: Ondal Medical Systems GmbH, Hünfeld (DE)

( * ) Notice: Subject to any disclaimer, the term of this patent is extended or adjusted under 35 U.S.C. 154(b) by 130 days.

(21) Appl. No.: 17/428,933

(22) PCT Filed: Feb. 6, 2020

(86) PCT No.: PCT/EP2020/053050
§ 371 (c)(1),
(2) Date: Aug. 5, 2021

(87) PCT Pub. No.: WO2020/161268
PCT Pub. Date: Aug. 13, 2020

(65) Prior Publication Data
US 2022/0128193 A1    Apr. 28, 2022

(30) Foreign Application Priority Data
Feb. 6, 2019    (EP) ..................................... 19155829

(51) Int. Cl.
*F16M 11/28*    (2006.01)
*F16M 11/20*    (2006.01)

(52) U.S. Cl.
CPC ......... *F16M 11/28* (2013.01); *F16M 11/2014* (2013.01); *F16M 2200/027* (2013.01); *F16M 2200/068* (2013.01)

(58) Field of Classification Search
CPC ......... F16M 2200/068; F16M 11/2014; F16M 11/08; F16M 11/04
(Continued)

(56) References Cited

U.S. PATENT DOCUMENTS

| 5,937,073 A  * | 8/1999 | Van Gieson ........... H04R 1/026 381/387 |
| 2004/0245424 A1 * | 12/2004 | Kuhn ..................... F16M 13/02 248/327 |

(Continued)

FOREIGN PATENT DOCUMENTS

| CN | 202521191 U | 11/2012 |
| GB | 2475298 A | 5/2011 |
| KR | 20120115830 A | 10/2012 |

OTHER PUBLICATIONS

International Search Report and Written Opinion for International Application PCT/EP2020/053050 dated Mar. 6, 2020, with English Translation, 9 pages.

*Primary Examiner* — Christopher Garft
(74) *Attorney, Agent, or Firm* — Seed IP Law Group LLP

(57) ABSTRACT

The invention relates to a fall arrester device (20) for a carrier system (10) for preferably movably holding at least one medical equipment, comprising at least one carrier device which has at least one critical point (12), and comprising at least one elongate securing part (22), wherein the carrier device has a first through-opening (24) in a first region (14) which is spaced apart from the critical point (12), and a second through-opening (26) in a second region (16) which is opposite to the first region with respect to the critical point (12) and is spaced apart from the critical point, (Continued)

Figure 1:
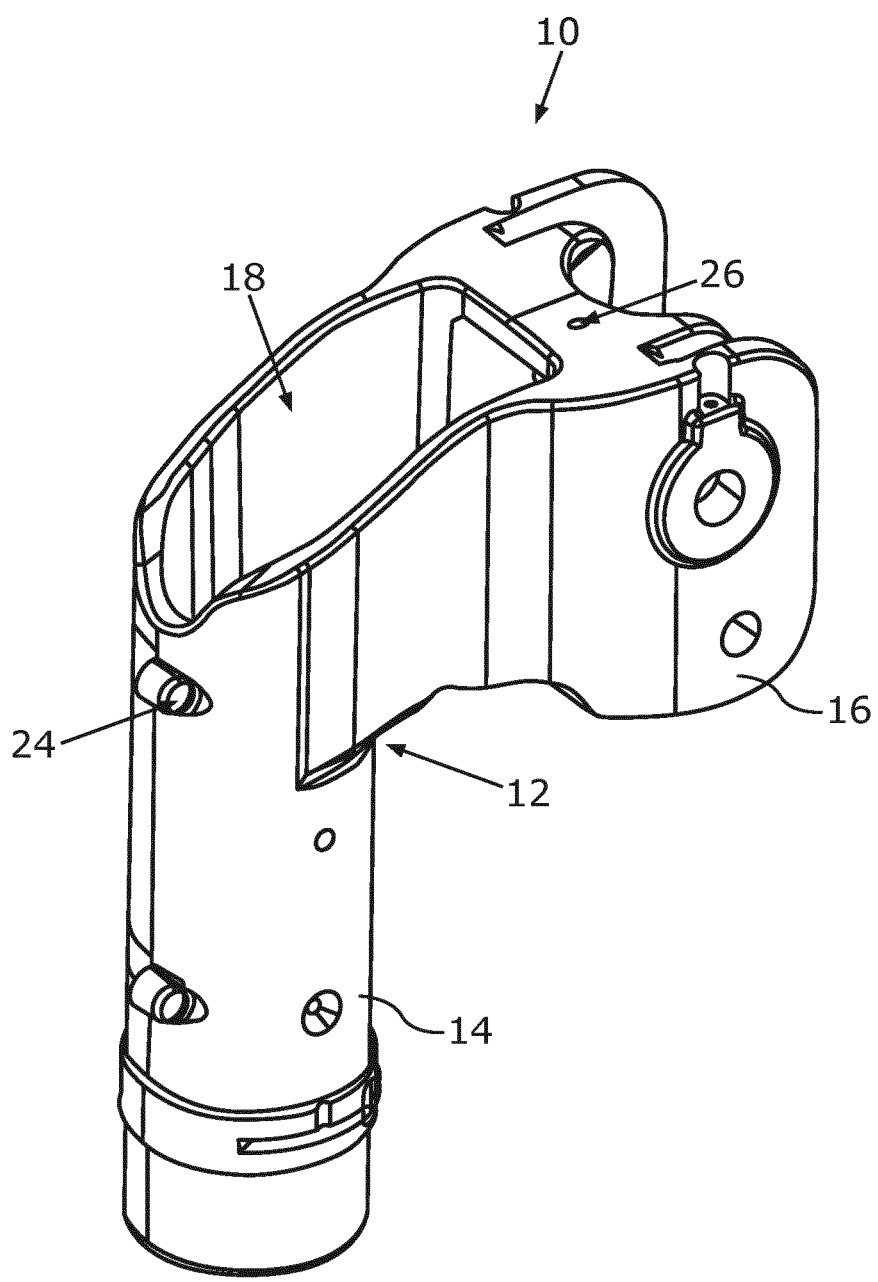

wherein the securing part (22) is routed through both through-openings (24, 26), and the fall arrester device (20) comprises a first blocking element (28) which is fastened to a first end of the securing part (22), and a second blocking element (30) which is fastened to a second end of the securing part (22) which is opposite to the first end of the securing part (22), wherein the two blocking elements (28, 30) are arranged in a way that the securing part (22) is blocked from sliding out of the two through-openings (24, 26).

17 Claims, 2 Drawing Sheets

(58) Field of Classification Search
USPC .................................................... 248/274.1
See application file for complete search history.

(56) References Cited

U.S. PATENT DOCUMENTS

2009/0173856 A1    7/2009  Auger et al.
2011/0309041 A1*  12/2011  Amadio ................ F16M 11/10
                                                           211/26

\* cited by examiner

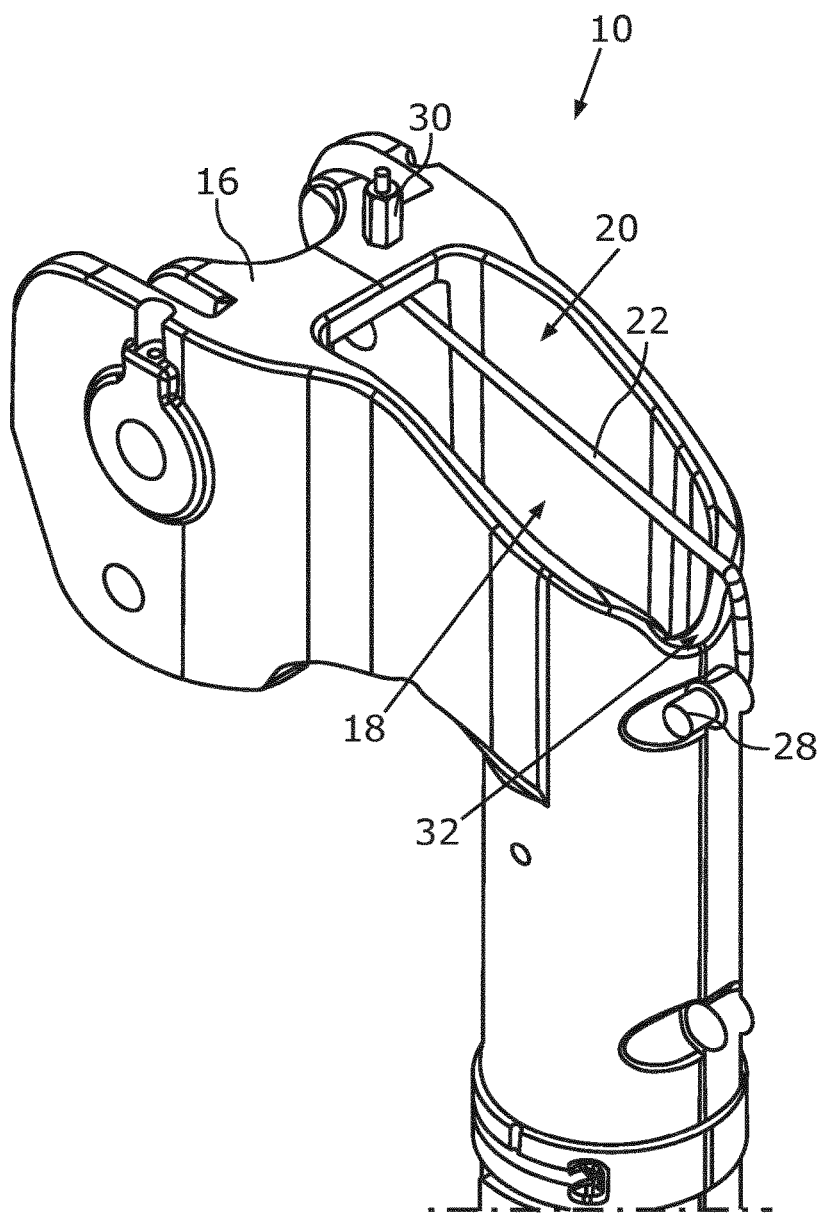
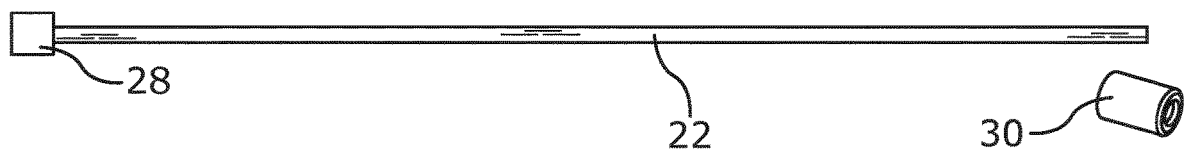
Fig.2
Fig.3

FALL ARRESTER DEVICE FOR A MEDICAL CARRYING SYSTEM, CARRYING SYSTEM FOR A PIECE OF MEDICAL EQUIPMENT, METHOD FOR ATTACHING A FALL ARRESTER DEVICE TO A CARRYING SYSTEM

The present invention relates to a fall arrester device for a carrier system for holding at least one medical equipment, a carrier system for a medical equipment, and a method for attaching a fall arrester device to a carrier system for a medical equipment.

Carrier systems are used in surgery rooms, for example, for holding a medical equipment in a locally displaceable or locally fixed way. Hereto a carrier arm may be movably anchored by means of a bearing assembly on a ceiling, a wall, or a floor, for example. A fastening to a frame including roles is also possible. A carrier system comprising carrier arms may also be denoted as a carrier arm system, and a carrier system which is configured for holding medical equipment may also be denoted as medical carrier system. In general, carrier systems comprise at least one movable carrier arm for holding the medical equipment, which may also be denoted as medical engineering equipment, for example a surgery lamp, a surgical kit or dental drill sets. In addition, the respective carrier arm systems may also comprise at least one brake device, which is configured to set a position of the carrier arm and thus of the medical equipment, and/or to inhibit respective movements of the carrier arm and thus of the medical equipment. The local displacement of medical equipment is vital for many medical procedures in order to facilitate or generally enable the work of medical staff.

Due to a frequent movement of single parts of the carrier system and/or by attaching different equipment, such a system and the parts thereof become heavily loaded. Due to market observation it could here be determined that the handling of such carrier arm systems by the users becomes more robust. In particular, joints are more heavily loaded by dynamic forces introduced by the users, and said loads of medical carrier arm systems caused by the operating staff may even increase further. More frequent and/or stronger movements may result in structural fatigue phenomena, and as a result breaks may occur on especially loaded elements or points of force application. In addition, weights which are frequently changed and/or a high weight of the respective medical equipment more and more impact the structural integrity of the carrier system over the lifespan thereof. In addition, misuse may occur in the course of time-consuming emergency surgeries or also in the normal operations in stream-lined hospital processes, and thus to loads exerted on the medical carrier system, by improper leaning against the carrier system or climbing on parts thereof by people, for example. A countermeasure hereto may be mechanically more robust constructions.

However, parts of the carrier system may break during a continuously improper and robust use, in particular on points of force application which are loaded to the maximum. Despite that, broken parts are never to endanger patients or medical staff. Due to this reason, a fall arrester device may be provided for medical carrier systems, which reliably prevents falling down of parts also during a break, and thus enables a secure usage of the carrier system also over a long usage period, even in case of improper use. A falling down of broken parts and a bouncing up of the remaining carrier arm may thus be prevented. At the same time it is and has to be easily evident to the user that a replacement or repair of the system is required after a break of the device. In any case, a continued usage of a system which is damaged in such a way is nearly impossible.

Such a catch device which is denoted as a fall arrester device is for example known from DE 100 51 898 B4. Regarding this, it is provided to wrap a securing loop around a bolt, wherein the securing loop comprises respective enlargements on the ends thereof, and engages through respective openings formed in a retaining body with said ends. Said retaining body may be detachably coupled to a main body. However, said fall arrester device requires a plurality of parts, and is thus accordingly complicated to manufacture, difficult to mount, extremely heavy and expensive in manufacturing as a whole. In addition, a respective installation space and fastening capabilities have to be provided for the different parts and for attachment thereof.

It is an object of the present invention to provide a simple and cost-efficient fall arrester device for a medical carrier system.

The object is achieved according to the invention by means of the subject-matters of the independent claims. Advantageous embodiments and purposeful further developments of the invention are specified in the respective dependent claims, wherein advantageous embodiments of an aspect may be regarded as advantageous embodiments of respective other aspects and vice versa.

A first aspect of the invention relates to a fall arrester device for a carrier system for preferably movably holding at least one medical equipment. The medical equipment may be a tray for a surgery kit, medical drilling sets, monitoring devices, and monitors, or a surgery lamp, for example. The carrier system may comprise a plurality of carrier arms, for example, and may for example be self-supported or may be mounted to a wall or ceiling. The carrier arms may be movably supported on each other in order to set the position of the medical equipment in a largely free way. The carrier system and/or the fall arrester device may at least comprise a carrier device by means of which the medical equipment is held. The carrier device may also comprise respective parts by means of which the medical equipment may be held spaced apart from the floor.

In general, movably holding does precisely not represent any fixed screwing of components.

The carrier device may comprise a critical point. For example, the critical point is defined as a point or region, where the carrier device is especially susceptible to breaking, for example during continued robust or improper use and/or unusual overloading. For example, the critical location or the critical point may be the one or one of the most loaded location(s), or the most loaded point(s) or one of the most loaded point(s) during proper and/or improper usage of the carrier device, that is the point(s) of force application in the carrier device where peaks of force occur, and thus breaks due to fatigue may occur with a higher probability. For example, the critical point(s) may be identified by structural calculations, by experiments and/or based on empirical values, or may also be provided as a predetermined breaking point in the structure of the carrier device which is specified by design.

The fall arrester device serves to prevent the predetermined break risk of parts of the carrier device. It may comprise an elongate securing part. By means of said securing part respective regions of the carrier device, which would be separated by a break at a critical point, may be additionally coupled to each other. This way, falling down of one of the two broken parts may be prevented even at a break at a critical point. Hereto, the securing part is coupled to or may be preferably coupled to the carrier device on both sides of the critical point, respectively. The securing part is preferably configured in a way that it is able to hold a part, which is broken at a critical point including a medical equipment fastened thereon, also during a certain fall distance. The fall distance may be limited by the length of the securing part. The fall arrester device may thus help to secure a critical point, and/or a predetermined breaking point introduced during manufacturing.

Further, the carrier device may comprise a first through-opening in a first region which is spaced from the critical point. Further, the carrier device may comprise a second through-opening in a second region which is spaced from a critical point. The second region is arranged opposite to the first region with respect to the critical point. A critical point may also be considered as a separation between the first and second region. In particular, a critical point may be considered as a continuous area through the carrier device, which divides it in two parts, in particular when a break of the carrier device at the critical point occurs. In the one part thus the first region, and in the other part the second region is arranged. The respective regions may here also be formed as end regions of the carrier device and/or correspond to a respective element of the carrier device, for example a carrier element, like a carrier arm. Preferably, the respective through-openings are spaced from a critical point to such a distance that the walls of the through-openings are not impacted by the break at a break on a critical point, the thickness or strength thereof are such, respectively, that the broken part may be held at the through-openings by using the securing part.

The securing part may be routed through both through-openings. In addition, the fall arrester device may comprise a first blocking element which is fastened to a first end of the securing part, and a second blocking element which is fastened to a second end of the securing part opposite to the first end. The blocking elements may be thus arranged in such a way that a sliding of the securing part out of the two through-openings is blocked. Correspondingly, the securing part may thus be fastened to the two through-openings. Thus, the two break parts are kept coupled to each other when a break occurs at the critical point by means of the securing part which is held on the through-openings. This way, a falling down of the broken part, or of a carrier arm, respectively, may reliably be prevented.

The fall arrester device needs only a few parts. In particular, the respective fastening bolts and/or loops may be waived. This way, the fall arrester device is lightweight and cost-efficient. In addition, the fall arrester device needs only installation space for routing the securing part from one through-opening to the other, and no additional installation space for anchoring is required, thus said installation space is available for other parts. The blocking elements may be arranged on the outside on the carrier device, for example. In addition, mounting of the fall arrester device is very simple, as a first free end may be routed through the two through-openings, and then a blocking element may be fastened to the free end, for example. In addition, a backlash-free mounting may be readily achieved, as a subsequent attachment of the blocking element enables a simple alignment to the actual distance between the two through-openings The securing part may also be set as being tensioned on the carrier device, or the two through-openings, respectively. A small backlash minimizes a falling distance at a break of the carrier device, and thus additional dynamic fall loads to which the securing part and respective walls forming the through-openings have to be adapted. A projecting length of the securing part may be cut off after attachment, for example. The securing part may also be provided in a cost-efficient way having large manufacturing tolerances or as an endless component which may be cut as needed.

In a further advantageous embodiment of the fall arrester device, the fall arrester device is configured in a way that the securing part is load-free during usage of the carrier system, in particular before a break occurs at the critical point. Load-free may for example denote that the securing part does not contribute or contributes only a neglectable amount to receive a load of the held medical equipment. For example, also none of the two regions of the carrier system may be held by the securing part before a break of the critical point occurs. For example, a central region of the securing part may have a length which is larger than a shortest connection between the two through-openings. The securing part may for example be arranged in a partly hanging way and/or tension-free between the through-openings. Only after a break of the critical point, the securing part receives the weight of the medical equipment and of respective partial regions of the carrier system which have been broken and are hanging thereon. Due to the fact that the securing part is load-free, it is not subjected to any loads during proper use and/or improper use of the carrier arm system, provided that the critical point has not yet been broken. Before a break of the critical point, the load-free securing part does not hold two parts of the carrier system together or fastens them to each other, for example. This way, a material fatigue and/or wear of the securing part may be prevented before a break occurs at the critical point.

Preferably, the securing part has a diameter along its longitudinal extension which is smaller than the respective diameter of the through-openings. Preferably, the blocking elements are arranged on sides facing away from each other, wherein sides facing each other are defined by the two sides from which the securing part extends from one through-opening to the other through-opening.

The carrier device may also comprise a plurality of critical points. In said case, a securing part may be provided having two associated through-openings for each critical point which are arranged on both sides of the critical point, respectively. This way, the securing part and respective walls may be configured as adapted to the load case at a break of each single critical point. In addition, the fall distance may thus be especially small. However, it may also be provided that a common securing part and a corresponding pair of through-openings is provided for a plurality of critical points. In said case, the plurality of critical points may be considered as a common critical point as a whole, for which a through-opening has to be provided on both sides thereof, respectively. This way, the number of parts for the fall arrester device may be especially low. Hereby, the securing part and respective walls forming through-openings are to be adapted for a break of that point of the plurality of critical points where the highest load is to be expected.

A further advantageous embodiment of the fall arrester device provides that the critical point is a joint of the carrier device, a bearing between two parts of the carrier device, on which they are movably connected to each other, an angular piece of the carrier device, and/or a junction, in particular a weld, of the carrier device. This way, said expensive and/or heavy components may be configured in a simpler design and with reduced costs, as required, as people are always protected by the fall arrester device in case of a break of the carrier device. Thus, it becomes also possible to waive complex structural calculations, and in particular fatigue calculations. Alternatively or in addition, the critical point may be a structural weak or most weak region of the carrier device. Alternatively or in addition, the critical points may also be one or more points in the carrier arm device which are susceptible to break, which are exposed to force peaks, during proper and/or improper use. In addition, wear and/or fatigue may be taking into account when determining potentially critical points a priori. For example, a critical point may be considered as a region of the carrier element which has a thinner wall than other regions and/or carrier elements. In addition, a predetermined breaking point predefined by design may also be provided as critical point. Here, also load calculations and fatigue calculations may be taken into account to determine useful points, where a fall protection has to be provided.

A further advantageous embodiment of the fall arrester device provides that the elongate securing part is configured as flexible element. This way, the securing part may be routed through the through-openings in an especially simple way. In addition, in case the through-openings are not arranged on a line, but are connected across edges, for example, mounting is also facilitated. In addition, the flexible element may also adapt its shape in case the two through-openings are moved towards each other. This is for example often the case, when the securing part secures a bearing or a joint as critical point. A simple and cost-efficient example for a flexible element is a rope, which may also be denoted here as a catch rope. The rope may for example be a metal rope, like a steel rope, or a plastic rope or may be formed from natural fibers. As alternative to a rope, a metal wire, or a flexible plastic part, such as a plastic bar, may be provided, for example.

A further advantageous embodiment of the fall arrester device provides that the first blocking element is fixedly coupled to the securing part and/or is formed integrally therewith as one single part. This makes mounting of the securing part especially simple, as an accidental withdrawal of the securing part from one of the two through-openings when inserting it into the other through-opening is prevented by the blocking element which is already attached. In addition, it is thus at most necessary to attach one of the blocking elements during assembly or mounting of the carrier system or of the fall arrester device, for example, which makes assembly and mounting fast and easy. The fixed blocking element may be injected, molded, welded, or also bonded, for example. The fixed blocking element may for example be injected as plastic nipple on the securing element formed as wire rope. Such a design is especially cost-efficient to manufacture.

A further advantageous embodiment of the fall arrester device provides that the second blocking element is configured to be only fastened to the securing part after the securing part has been routed through the two through-openings. This way, at first a free end of the securing part is available, which may simply be inserted through the two through-openings one after the other. After routing of the securing part through the through-openings, the second blocking element may permanently, that means fixed, or also detachably be fastened to the free end in order to fasten the securing part on both sides of the critical point and thus the potential breakpoint to the carrier device. A simple example for a detachable fastening is a screw connection of the second blocking element. Thus, by a releasable fastening, the fall arrester device and thus also the carrier system may be disassembled again in a simple and non-destructive way. Alternatively, the second fastening element may also be permanently and destructively, respectively, fastened in a detachable way. For example, the second fastening element may be bonded, soldered, welded, crimped, or pressed thereon. In particular, pressing thereon may for example be performed manually, by using a gripper, for example. This way, the fall arrester device may be easily mounted at site after assembly of the carrier system. Due to the permanent fastening, in particular an inadvertent detaching of the fall arrester device may be prevented.

Respective blocking elements may also be formed by the securing part itself, thus the number of parts may be especially small. For example, the blocking element may be formed for a rope-like securing part by a node in the rope. The securing part may also comprise flexible parts at the end, for example, which may be adjusted for providing the blocking feature.

A further advantageous embodiment of the fall arrester device provides that the respective blocking elements are configured in a way not to be able to slide through the respective associated through-openings. For example, the blocking elements formed as sleeve or nipple may be fitted over an end region of a securing part formed as a catch rope. Preferably, the size and form of the respective blocking elements is configured in a way that they do not fit through the through-openings. For example, a sleeve and/or nipple may have a diameter which is greater than a diameter of the respective through-openings. The blocking elements may also be formed as thickened ends of the securing part, in particular as thickened ends of a catch rope.

A further preferred embodiment of the fall arrester device provides that the carrier device delimits an interior space and at least one of the through-openings extend from the interior space to the outside, that is outside of the interior space, for example to an outer side of the carrier device. This way, the securing part may be routed to an outside of the carrier device, thus it may be accessed for mounting of the blocking element, in particular to the free end, during mounting. By at least one part attached on the outside, as for example a region of the securing part and/or of one of the blocking elements, it may also be easily checked visually that the fall arrester device has actually been attached to the carrier system. Preferably, both through-openings extend from an interior space to the outside, thus mounting of the securing part may be especially simple performed from outside. The through-openings may preferably be provided in a wall or walls delimiting the interior space. In addition, the respective blocking elements do thus not need an installation space within the carrier device. This may then be used for conduits, for example. The securing part may then be routed at least partly on the inside to protect it against damage. Precisely a flexible securing part may thus easily adapt the form thereof to an available inner passage. The interior space may be completely closed. Alternatively, the interior space may also be open to one side or may be configured as a through-opening type. For example, the carrier device often comprises one or more hollow profile(s) which constitute respective carrier arms and the interior space. The interior passage of said hollow profiles may here be connected to an outside of the hollow profile by one or each of the two through-openings.

Due to the construction of the fall arrester device, only a central part of the securing part may be arranged in the interior space of the carrier device, and the two blocking elements on the outer side or vice versa, for example. As compared to a retaining body, the interior space is not quite completely occupied, but only a little bit downsized. No bolts or retention bodies are used which occupy installation space in the interior space, but through-openings which rather tend to provide additional installation space. This way, cables may be passed here through, for example, data conduits and/or a power supply for the medical equipment, for example. In addition, the fall arrester device does not block any mounting and/or routing of slip rings on a joint.

A further advantageous embodiment of the fall arrester device provides that at least one of the two blocking elements is arranged outside of the interior space. Preferably, the two blocking elements are arranged outside. This way, for example, the usually slimmer and also preferably flexible securing part may be arranged mostly inside, thus especially much installation space is available for the parts in the interior space, wherein the securing part may align itself to the inner form in a protected way.

A further advantageous embodiment of the fall arrester device provides that at least one central region of the securing part is arranged within the interior space. Only respective ends including the blocking element are arranged correspondingly outside of the interior space.

A second aspect of the invention relates to a carrier system for holding at least one medical equipment. Said carrier system comprises a fall arrester device according to a first aspect of the invention. Preferably, the carrier system is configured to movably hold the medical equipment. In addition, the carrier system may comprise one or more carrier arms, and may correspondingly be denoted as carrier arm system. The features and advantages resulting from the fall arrester device according to the first aspect of the invention are detailed in the specification of the first aspect of the invention, wherein advantageous embodiments of the first aspect of the invention are to be regarded as advantageous embodiments of the second aspect of the invention and vice versa.

A further advantageous embodiment of the carrier system provides that the carrier system comprises at least one first carrier element, in particular a first carrier arm, and a second carrier element, in particular a second carrier arm, which are preferably coupled to each other by means of a joint, wherein the first carrier arm includes the first through-opening, and the second carrier arm includes the second through-opening, through which the securing part is routed, respectively. The joint may here form the critical point, the break thereof is secured by the fall arrester device. The joint may preferably or basically be made of steel or aluminum, for example. It may be a cast part. Alternatively, the joint part may also be made of plastic or a plastic-composite-material. This way a simple, cost-efficient, and easy to mount carrier system is provided, for which a falling down of a broken part or a part due to a break of a joint is prevented by the securing part and the blocking elements.

A third aspect of the invention relates to method of attaching a fall arrester device to a carrier system, preferably for movably holding of at least one medical equipment. In particular, this may be a method for mounting the fall arrester device according to the first aspect or a method which is suited for attachment thereof. In addition, it may also be a method for mounting the fall arrester device, in particular the fall arrester device according to the first aspect of the invention, to the carrier system according to the second aspect of the invention. The features and advantages resulting from the fall arrester device according to the first aspect of the invention and the carrier system according to the second aspect of the invention are detailed in the specification of the first and/or second aspect of the invention, wherein advantageous configurations of the first and second aspects of the invention are to be regarded as advantageous configurations of the third aspect of the invention and vice versa.

The method may comprise the step of providing at least one elongate securing part having a first blocking element fastened to the first end and a second free end opposite to said first end, and providing at least one carrier device having at least one critical point, a first through-opening in the first region spaced from said critical point, and a second through-opening in a second region spaced from said critical point, which is arranged opposite to said first region with respect to said critical point. In a further step, the free end of the securing part is routed through the two through-openings, in particular one after another. Subsequently, fastening of a second blocking element to the free end may be performed, thus a sliding of the securing part out of the two through-openings is blocked. Such a mounting is fast and easy. In addition, a sliding out of the securing part on the through-opening, through which it has first been routed, is prevented by the already mounted blocking element when routing it through the other through-opening.

Preferably, the second blocking element is thus positioned along the elongate securing part, thus the securing part is positioned and/or is tensioned between the two through-openings nearly without any backlash. Without any backlash may denote here in particular that the securing part may not be moved or is only movable to a small degree along the longitudinal extension thereof. This way, a fall distance during break of the critical point may be minimized. An end of the securing part eventually projecting beyond the blocking element may then be separated after attaching of the blocking element.

In addition, a later attachment or retrofitting of the fall arrester device to an already existing carrier system may easily be performed. Hereto, respective, not yet existing through-openings may subsequently be inserted, for example. For example, in two carrier arms which are coupled by means of a joint, holes may simply be drilled as through-openings, respectively, through which the securing part may then be routed.

A further advantageous embodiment of the method provides that the second blocking element is configured as a sleeve which is fitted on the free end on the securing part for fastening and is pressed therewith. This way, the securing part may easily be defined thereon after routing through the two through-openings by using a simple tool.

Further features of the invention become apparent from the claims, the exemplary embodiments, and the figures. The features and the combination of features mentioned in the specification above and the features and combinations of features mentioned in following exemplary embodiments may be used not only in the respective specified combination, but also in other combinations within the scope of the invention.

Here shows:

FIG. 1 in a partial schematic perspective view a carrier arm system for a medical equipment including one joint;

FIG. 2 in another schematic perspective view the carrier arm system according to FIG. 1 including only one fall arrester device mounted thereon; and FIG. 3 in a schematic view which additional parts are required for providing a fall arrester device to the carrier arm system according to FIG. 1.

FIG. 1 shows a partial schematic perspective view of a carrier system 10, configured as a carrier arm system, for a medical equipment, which is not shown, including a carrier device, which comprises two carrier elements 14 and 16 which are movably connected to each other by means of a joint 12. Alternatively, the joint 12 may also be formed as an angular piece and couple the two carrier elements 14, 16 rigidly with each other.

The carrier element 14 is here configured to hold the medical equipment at the lower end thereof, for example a surgery light, a surgery device and/or a dental drilling set. The carrier element 14 may here be rotated against the carrier element 16 due to the joint 12 in order to set the alignment of the medical equipment. The carrier element 16 is configured on the end thereof which faces away from the joint 12 to be coupled to a carrier arm of the carrier system 10. Said coupling may also comprise a joint to provide a further degree of freedom for setting the position of the held equipment.

The carrier element 14 is formed as a hollow profile by which the respective cables for power supply of the medical device may be routed. The carrier element 14 and the carrier element 16 are also connected electrically to each other by means of a sliding contact on the joint 12. In addition, the carrier element 16 comprises at least one partially delimited interior space 18 in which additional parts and cables for current-supply may be installed. The interior space 18 may thus be closed by a not-shown closure cap which snaps into the carrier element 16, for example.

Due to a frequent movement of the medical equipment and thus the movement of the carrier elements 14, 16 relative to each other, an unexpected strong fatigue of the joint 12 may occur. Further, a frequent change of the held equipment and/or improper loads may cause fatigue and/or overload of the joint 12. In addition, an alternatively provided angular piece may thus be overloaded and/or experience fatigue. The joint 12 or the angular piece are thus susceptible to high loads and are basically more susceptible to break than the carrier elements 14, 16, for example, and thus presents a critical point of the carrier system 10. Especially fatigue is not easily recognized here, thus an unexpected break of the joint 12 and a falling down of the medical equipment and of the carrier element 14 may occur during improper use and lacking maintenance over a long period of time. Here, said parts are not to fall down to a degree that a patient located under it or medical staff may be endangered. In addition, a falling down may damage the medical equipment and thus endanger a treatment.

Thus, the carrier system 10 comprises a fall arrester device 20, which is shown in the further perspective view of the carrier system 10 in FIG. 2. The fall arrester device 20 comprises a securing part 22 which is formed as a wire rope 22 hereto, by means of which the carrier elements 14, 16 may be connected to each other in addition to the joint 12. In case of a break of said joint 12, the carrier element 14 is thus further held on the carrier element 16, thus neither people nor the medical equipment are endangered.

Hereto, the carrier element 14 comprises a first through-opening 24, and the carrier element 16 a second through-opening 26. The wire rope 22 is routed through the two through-openings 24, 26. On a side facing away from the respective side of the walls which are coupled by the wire rope 22 which form the two through-openings 24, 26 a blocking element 28, 30 is arranged on each of the two through-openings 24, 26. By the two blocking elements 28, 30, the wire rope 22 is set to the two carrier elements 14, 16 on the through-openings 24, 26, and is secured against sliding off, and thus holds them together even in case the joint 12 is broken.

Regarding the joint 12, the two through-openings 24, 26 are thus arranged on regions facing away from each other, and in carrier elements 14, 16, respectively, facing away from each other with respect to the joint 12 on both sides thereof and are spaced from joint 12. Due to said spacing, the through-openings 24, 26 are not susceptible to a break of the joint 12 and thus to release the wire rope 22.

As may be seen in FIG. 1, the through-opening 26 is drilled through a wall of the carrier element 16, which at least partly delimits the interior space 18. This way, the wire rope 22 may be routed through the interior space 18 under a closure cap in a protected way. In contrast thereto, the rigid blocking element 28 is arranged outside of the interior space 18 and does not occupy any space. The drilling may thus also subsequently easily be inserted in the carrier element 16.

As may also be seen in FIG. 1 and FIG. 2, the through-opening 24 is formed by drill hole which may also be used as a screw connection of two shells of the hollow profile of the carrier element 14. By a rigid pretensioned fastening of the wire rope 22, there is no screw connection required at said location. The wire rope 22 is then holding the two shells together there. This way, the fall arrester device may be retrofitted here, without having to insert an additional drill hole into the carrier element 14. Also, the blocking element 30 is arranged outside on the carrier element 14. By arrangement of the two blocking elements 28, 30 on the outside it may easily be checked visually whether the fall arrester device 20 has been actually attached. In addition, mounting is especially simple.

On the carrier element 14, the wire rope 22 is routed on a recess 32 into the interior space. Said recess may be designed for detaching the not-shown closure cap, for example. Thus no additional passage for the wiring rope 22 has to be provided in order to enable it to be also partially routed in the interior space 18 when using the through-opening 24 serving as screw connection.

FIG. 3 schematically shows the required parts for providing a fall arrester device compared to a conventional carrier system. In the shown example, the blocking element 28 is a nipple which is injection molded on the wire rope 22, for example a nipple made of plastic. This way, the diameter on said end of the wire rope 22 is larger than that of the through-openings 24, 26. Contrary, the wiring rope 22 is provided without any blocking element at the other end. Said free end may respectively be inserted through the through-openings 24, 26 for attaching the fall arrester device. Subsequently, the separate blocking element 30 may be mounted on said end to the wiring rope 22 in order to set it on the two carrier elements 14, 16, and couple them to each other in addition to the joint 12.

In FIG. 3 in the present embodiment, the blocking element 30 is shown as a sleeve including a through-opening as an example. Said sleeve may be fitted on the wire rope 22 and may be pressed to define the axial position thereof, for example by using a gripper. Thus, the sleeve is easy to mount. Subsequently, a projecting part of the wire rope 22 may be cut off. Alternatively, as shown in FIG. 2, the blocking element 30 may also be screwed on. Hereto, the wire rope 22 may comprise a threaded region, or the blocking element may cut such a thread into the wire rope 22. Advantageously, the securing part 22 may also be formed as a metal wire in this case. In the example shown in FIG. 2, the blocking element 30 is formed including an outer hexagon bolt for an easy engagement of the tool.

As can be seen, the fall arrester device 20 is easy to attach, requires only a few additional parts, which in addition are lightweight and cost-efficient, and blocks nearly no installation space in the interior space 18 of the carrier system 10. In addition, standard products may be used as parts of the fall arrester device 20 which are inexpensive to manufacture, and do not have to be specifically aligned to the geometry of the carrier elements 14, 16.

LIST OF REFERENCE NUMBERS

10 Carrier system
12 Joint
14 Carrier element
16 Carrier element
18 Interior space
20 Fall arrester device
22 Securing part/wire rope
24 Through-opening
26 Through-opening
28 Blocking element
30 Blocking element
32 Recess

The invention claimed is:

1. A carrier system for movably holding at least one medical equipment using at least one fall arrester device, comprising:
   at least one carrier device which comprises at least one critical point, and having at least one elongate securing part,
   wherein the at least one carrier device comprises a first carrier arm having a first through-opening in a first region which is spaced apart from the at least one critical point, and comprises a second carrier arm having a second through-opening in a second region which is opposite to the first region, the first and second through-openings located on opposing regions with respect to the at least one critical point and are spaced apart from the at least one critical point,
   wherein the at least one fall arrester device comprises:
      the at least one securing part which is arranged between the first and second regions and routed on a recess of the first region and through the first and second through-openings,
      a first blocking element which is fastened to a first end of the at least one securing part,
      a second blocking element which is fastened to a second end of the at least one securing part which is opposite to the first end thereof, and
      wherein the first and second blocking elements are arranged in such a way that a sliding of the at least one securing part out of the first and second through-openings is blocked.

2. The carrier system according to claim 1, wherein:
   the at least one critical point is a joint of the at least one carrier device; and
   a bearing is positioned between two parts of the carrier device, where the two parts are movably connected to each other.

3. The carrier system according to claim 1, wherein the at least one elongate securing part is configured as a flexible element.

4. The carrier system according to claim 1, wherein the first blocking element is fixedly coupled to the at least one securing part or is formed integrally therewith as one single part.

5. The carrier system according to claim 1, wherein the second blocking element is configured to be only fastened to the at least one securing part after the at least one securing part is routed through the first and second through-openings.

6. The carrier system according to claim 1, wherein the respective first and second blocking elements are configured in a way not to be able to slide through the respective associated first and second through-opening.

7. The carrier system according to claim 1, wherein the at least one carrier device delimits an interior space and at least one of the first and second through-openings extends from the interior space towards an outside of the carrier system.

8. The carrier system according to claim 7, wherein at least one of the first and second blocking elements is arranged outside of the interior space.

9. The carrier system according to claim 7, wherein at least one central region of the securing part is arranged within the interior space.

10. The carrier system according to claim 1, wherein the fall arrester device is configured in a way such that the at least one securing part is load-free during usage of the carrier system before a break occurs at the at least one critical point.

11. The carrier system according to claim 2, wherein the joint of the carrier device is formed as a cast component made of aluminum or steel.

12. The carrier system according to claim 1, wherein the first carrier army and the second carrier arm are moveably coupled to each other by a joint.

13. A method for attaching a fall arrester device to a carrier system for movably holding at least one medical equipment comprising at least the following:
   providing at least one elongate securing part having one first blocking element which is fastened to a first end, and a second free end opposite to the first end;
   providing at least one carrier device, which comprises at least one critical point, a first through-opening in a first region which is spaced apart from the at least one critical point, and a second through-opening in a second region which is opposite to the first region, the first and second through-openings located on opposing regions with respect to the at least one critical point and is spaced apart from the at least one critical point;
   routing the free end of the said at least one securing part on a recess of the first region and through the first and second through-openings; and
   fastening of a second blocking element to the free end, thus a sliding of the securing part out of the first and second through-openings is blocked.

14. The method according to claim 13, wherein the second blocking element is configured as a sleeve which is fitted on the free end on the at least one securing part for fastening and is pressed therewith.

15. The carrier system according to claim 2, wherein the joint of the at least one carrier device is an angular piece of the carrier device or a region of the carrier device coupling the first and second regions of the carrier device rigidly with each other.

16. The carrier system according to claim 5, wherein after the at least one securing part is routed through the first and second through-openings, the second blocking element is detachably fastened to the free end in order to fasten the at least one securing part on both sides of the at least one critical point.

17. A carrier system for movably holding at least one medical equipment using at least one fall arrester device, comprising:
   at least one carrier device which comprises at least one critical point, and having at least one elongate securing part,
   wherein the at least one carrier device comprises a first through-opening in a first region which is spaced apart from the at least one critical point, and comprises a second through-opening in a second region which is opposite to the first region, the first and second through-openings located on opposing regions with respect to the at least one critical point and is spaced apart from the at least one critical point, wherein the at least one securing part is arranged between the first and second regions and routed on a recess of the first region and through the first and second through-openings, and the fall arrester device comprises a first blocking element which is fastened to a first end of the at least one securing part, and a second blocking element which is fastened to a second end of the at least one securing part which is opposite to the first end thereof, wherein the first and second blocking elements are arranged in such a way that a sliding of the at least one securing part out of the first and second through-openings is blocked, and wherein the carrier system comprises a first carrier arm, and a second carrier arm, which are moveably coupled to each other by a joint, wherein the first carrier arm includes the first through-opening, and the second carrier arm includes the second through-opening, through which the at least one securing part is routed, respectively.

* * * * *